United States Patent [19]
Wakil et al.

[11] Patent Number: 5,970,984
[45] Date of Patent: Oct. 26, 1999

[54] METHOD OF REFRACTIVE SURGERY

[75] Inventors: Youssef Salih Wakil, Houston, Tex.; Spencer P. Thornton, Nashville, Tenn.; Ioannis G. Pallikaris, Voujes, Greece

[73] Assignee: Eyesys-Premier, Inc., Irvine, Calif.

[21] Appl. No.: 08/956,878

[22] Filed: Oct. 23, 1997

Related U.S. Application Data

[63] Continuation of application No. 08/355,436, Dec. 13, 1994, Pat. No. 5,722,427, which is a continuation of application No. 08/060,127, May 10, 1993, abandoned.

[51] Int. Cl.⁶ .................................................. A61B 19/00
[52] U.S. Cl. ........................................................ 128/898
[58] Field of Search ........................... 128/898; 606/166; 351/205, 206, 212; 600/300, 301

[56] References Cited

U.S. PATENT DOCUMENTS

| | | | |
|---|---|---|---|
| 4,340,059 | 7/1982 | Marinoff | 606/166 |
| 4,880,017 | 11/1989 | Soll et al. | 128/898 |
| 4,988,348 | 1/1991 | Bille | 606/5 |
| 5,219,344 | 6/1993 | Yoder, Jr. | 606/5 |

*Primary Examiner*—Mickey Yu
*Assistant Examiner*—Kelly O'Hara
*Attorney, Agent, or Firm*—Knobbe, Martens, Olson & Bear, LLP

[57] ABSTRACT

A novel method and apparatus is presented for the performance of refractive surgery. The success of refractive surgery, particularly astigmatic refractive surgery varies with the intuition and skill of the surgeon yielding a consistency of results more typical of art than science. In the described embodiments methods and apparatus that quantify refractive surgery by determining the nature of incisions are based upon traceable and repeatable factors. The described embodiments incorporate hardware and software for use in the data management.

6 Claims, 11 Drawing Sheets

| Arcuate Cuts Octical zone | Position 4mm |
|---|---|
| 1st Axis Cuts | 316-67 |
| 2nd Axis Cuts | 158-248 |

| Dioptric Power Optical zone | 4mm | |
|---|---|---|
| A: 1st Min | 43.72 | (110-116) |
| Mean A-B | 44.67 | (67-70) |
| B: 1st Max | 45.67 | (19-29) |
| Mean B-C | 44.88 | (316-316) |
| C: 2nd Min | 44.12 | (278-291) |
| Mean C-D | 45.12 | (248-249) |
| D: 2nd Max | 46.17 | (196-213) |
| Mean D-A | 44.91 | (156-158) |

| Arcuate Cuts Octical zone | Position 4mm | | 5mm | | 6mm | |
|---|---|---|---|---|---|---|
| 1st Axis Cuts | 316-67 | | 37-128 | | 39-127 | |
| 2nd Axis Cuts | 158-248 | | 218-312 | | 219-313 | |

| Dioptric Power Optical zone | 4mm | | 5mm | | 6mm | |
|---|---|---|---|---|---|---|
| A: 1st Min | 43.72 | (110-116) | 36.93 | (171-171) | 36.53 | (169-178) |
| Mean A-B | 44.67 | (67-70) | 38.86 | (128-129) | 38.66 | (127-128) |
| B: 1st Max | 45.67 | (19-29) | 41.01 | (77-85) | 41.01 | (81-91) |
| Mean B-C | 44.88 | (316-316) | 39.50 | (36-37) | 39.50 | (38-39) |
| C: 2nd Min | 44.12 | (278-291) | 38.09 | (347-359) | 38.05 | (346-358) |
| Mean C-D | 45.12 | (248-249) | 39.13 | (312-314) | 39.93 | (313-313) |
| D: 2nd Max | 46.17 | (196-213) | 40.23 | (266-272) | 39.85 | (268-276) |
| Mean D-A | 44.91 | (156-158) | 38.51 | (217-218) | 38.11 | (218-219) |

METHOD OF REFRACTIVE SURGERY

This is a continuation of application Ser. No. 08/355,436 filed Dec. 13, 1994, now U.S. Pat. No. 5,722,427 which is a file wrapper continuation of Ser. No. 08/060,127 filed May 10, 1993, now abandoned.

1. BACKGROUND OF THE INVENTION 1.1 The Field of Corneal Topography and Eye Surgery A. Corneal Measurement and Correction The corneal surface is responsible for the majority of the refractive power of the human eye. Therefore, measurement of the cornea's surface refractive power is very important in the diagnosis and treatment of many visual disorders. A common gauge of surface refractive power is the topography of the eye's cornea. Methods of ascertaining the eye's corneal topography are comprised of interferometric, rasterstereographic and videokeratographic technologies.

Corneal topography provides information about corneal curvature that allows ophthalmic surgeons to improve surgical results. A wide variety of surgical procedures currently benefit from pre and post surgical planning with corneal topography: astigmatic keratotomy (AK); epikeratophakia (EPI); radial keratotomy (RK); Excimer laser surgery; photorefractive keratectomy (PRK); penetrating keratoplasty (PK); Thermokeratoplasty (TKP) and cataract surgery.

1.2 The Problem of Quantifying Eye Surgery

A. Information in a Corneal Topography Map

Typically, the information provided by a corneal topography map is a set of curvature points that represent the corneal surface. Each point can indicate a specific radius of curvature or dioptric power at the correlative point on the examined eye. See e.g. Koch D. D., Foulks G. N., Moran C. T., Wakil J. S., "The Corneal EyeSys System: Accuracy Analysis and Reproducibility of First-Generation Prototype, "*Refract Corneal Surge.*, volume 5, pg 424–429, 1989.

The use of corneal topography for preoperative examination has greatly increased the accuracy, precision and amount of information in preoperative examination data. This data volume continues growing, following new developments in corneal modelling and corneal topographic measurements. See Koch D. D. supra; Belin M. W., Litoff D., Strods S. J., Winn S. S., Smith R. S., "The PAR Technology Corneal Topography System," *Refract Corneal Surg.*, 8: 88-96, 1992. Managing this volume of data is one of the barriers to the beneficial evolution of corneal shaping techniques. This barrier is most apparent with respect to certain techniques such as astigmatic arcuate cuts. See Lundergan M. K., Rowsey J. J., "Relaxing Incisions,"Corneal Topography." *Ophthalmology*, 92: 1226–1236 (1985).

B. Incisions and The Use of Corneal Topography

The use of corneal topography is becoming more and more prevalent in the field of incisional refractive surgery. Incisional refractive surgery (RK & AK) involves cutting the cornea to relax and flatten selected areas in order to achieve the desired vision correction without the need of corrective lenses (specifically, glasses or contact lenses). A refractive surgeon uses a corneal topography map to plan the location of cuts to be made in the eye during surgery. This planning process involves a study of the corneal topography map to determine areas of the cornea requiring topographic change. Given this information, the surgeon can estimate the size and position of one or more cuts that will correct the problem. This procedure is entirely subjective. While viewing a corneal topography map, a surgeon estimates the size and placement of a corrective incision relying on intuition and experience. While some surgeons may use some quantitative techniques, this process yields varying results because the size and location of the incisions cannot be precisely correlated to an invariant source. This is because the method of surgery represents an acquired intuition or art on behalf of the surgeon and not an exact scientific and quantitative approach or method. Therefore, the success of a particular surgery depends largely upon the skill and experience of the specific surgeon. Furthermore, even a specific surgeon's results may vary substantially from hour to hour or day to day.

2. SUMMARY OF THE INVENTION

An object of the current invention is to use a corneal topography map and known or derived quantitative factors in order to precisely indicate and quantify the size and position of corrective cuts for a variety of eye disorders. The invention includes a method and apparatus for achieving quantitative results in refractive surgery.

The invention contemplates the use of corneal topography to provide empirical data for use in surgical procedures. A corneal topography map can be used to produce dioptric power curves. A dioptric power curve is a graphical representation of the corneal surface at a specified radius from the vertex of the eye. Many dioptric power curves can be created for each corneal topography map (one at each discrete radius).

The dioptric power curve can be used to plan the size and location of corrective incisions. A horizontal line on the dioptric power curve can be used to indicate a target corneal shape. There are several methods of refractive surgery that can be based on the dioptric power curve: 1) using the mean dioptric power value between neighboring astigmatic axes; 2) using the area under the dioptric power curve with respect to the target line; 3) using the inflection points of the dioptric power curve with respect to the target line.

The invention further contemplates the use of certain patient factors along with the above identified methods. Patient factors are additional factors that influence the location and size of corneal incisions. The combination of patient factors and dioptric power curve analysis can yield a highly accurate and quantitative method of surgery patient factors.

The invention further contemplates the use of a computer program to resolve the procedures dictated. A computer program embodiment would allow the a method which accounts for all known possibilities and suggests the better possibilities for the planned surgery.

4. DETAILED DESCRIPTION OF SPECIFIC EMBODIMENTS

A. Dioptric Power Functions

Figure 1:
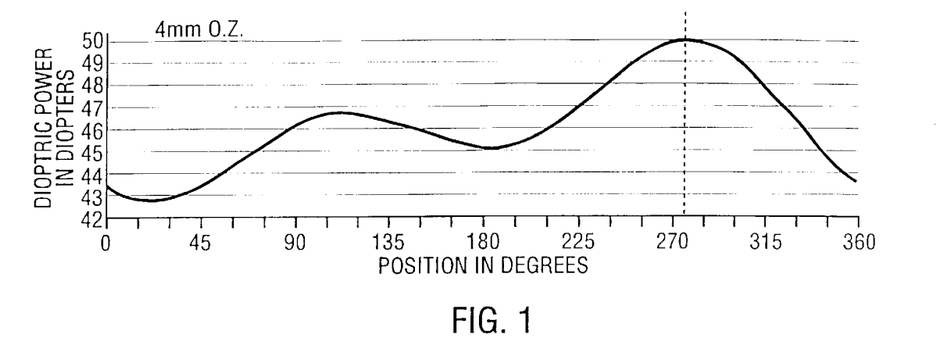
FIG. 1 is a dioptric power curve.

A dioptric power function graph is an alternate manner for displaying some of the information supplied by a corneal topography map. Quantitatively, this representation shows dioptric power at a specific diameter optical zone, as a function of radial position. For example, FIG. 1 is a dioptric power function taken at the 4 millimeter optical zone (4 mm oz). The abbreviation "oz" is used to indicate a circular optical zone with a specified diameter, centered at the vertex of the eye or visual axis. FIG. 1 shows that at 4 mm oz, and 275 degrees the dioptric power is 50 diopters.

The information in a dioptric power function can be extracted from the corneal topography map as follows: 1) a specific diameter optical zone is selected; 2) a reference for zero degrees of radial location is selected (conventionally, the right most point of an optical zone on the horizontal plane is designated as zero degrees); 3) the diopter power at zero degrees and at the selected optical zone is read from the corneal topography map (visually, with software or otherwise); 4) the diopter power information is plotted circumferencing from 0 to 359 degrees on a graph; and 5) a sufficient number of points are plotted to develop a diopter power curve of the desired resolution.

Figure 2:
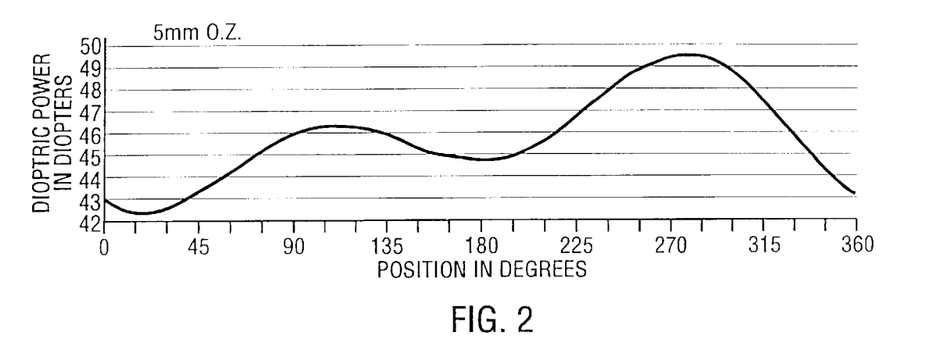
FIG. 2 is a dioptric power curve.
Figure 3:
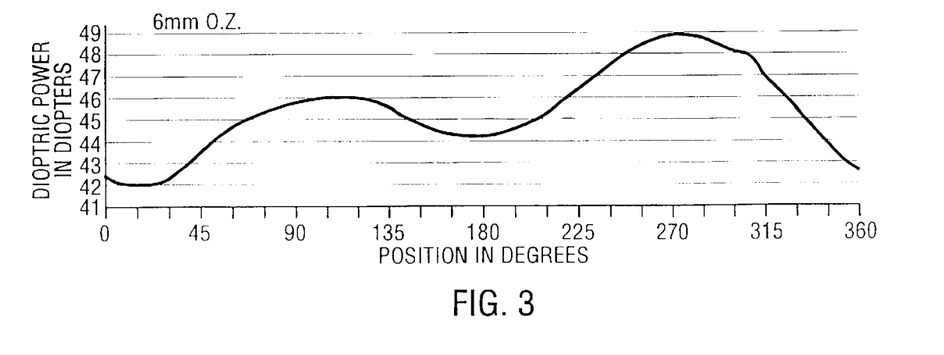
FIG. 3 is a dioptric power curve.

FIGS. 1, 2 and 3 are the dioptric power curves for the same eye, taken at different optical zone diameters. As shown in the diagrams: FIG. 1 is for a 4 mm oz; FIG. 2 is for a 5 mm oz; and FIG. 3 is for a 6 mm oz. Note the changing shape and amount of dioptric power as diameter increases. For example, FIG. 1 shows maximum diopter power of 50 at a location of approximately 275 degrees; FIG. 2 shows a maximum diopter power of 49.5 at approximately 272.5 degrees; and FIG. 3 shows a maximum diopter power of 48.7 at approximately 270 degrees.

Figure 4:
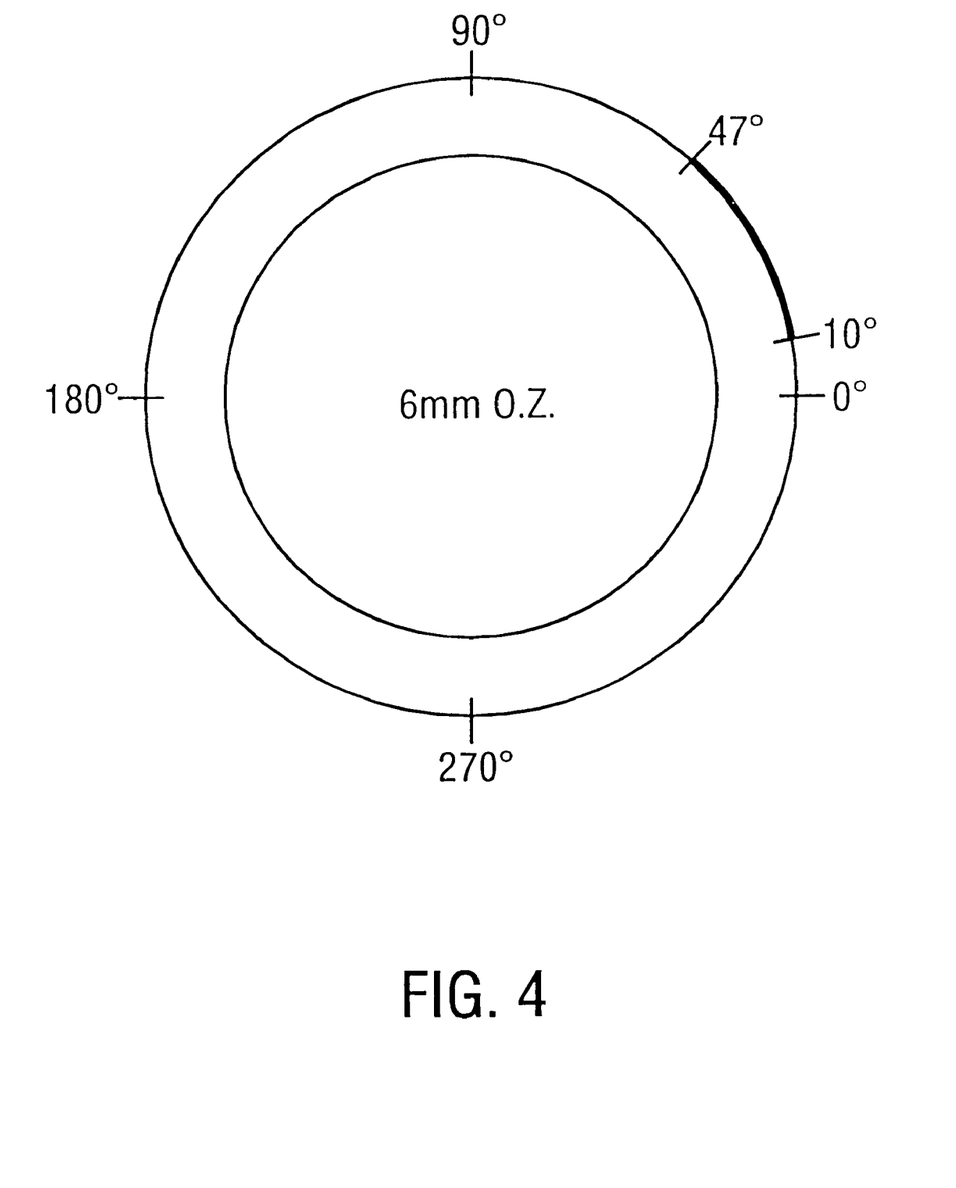
FIG. 4 is a an illustrative incision at the 6 mm optical zone.

B. Using the Diopter Power Curve to Derive the Size and Location of a Corrective Incision Once the dioptric power curve is created and understood it may be used as a basis for selection of the size and location of corrective incisions. Using the dioptric power function as a gauge allows a surgeon to correlate the size and location of corrective incisions with a quantifiable, invariant and repeatable standard. For example, a surgeon may analyze a plethora of dioptric power functions for a single eye. The surgeon might then use a quantifiable method to determine the size and location of one or more arcuate incisions that achieve the desired vision correction. For the purpose of this example, assume that the surgeon determines that one incision is sufficient and it should be an arcuate incision along the 6 mm oz from 10 degrees to 47 degrees. (see FIG. 4). The surgery is documented and repeatable because there is: 1) an invariant and repeatable basis (the dioptric power function); 2) a quantifiable method (discussed below); and 3) a specified incision location and size.

If the quantifiable method is taken from the surgeon and given to a computer then the number of factors and possible solutions can be increased dramatically. For example, a computer can consider many diopter power functions in conjunction with many patient factors. Furthermore, the computer can simulate the surgical results using several quantitative methods. The computer can then determine which method or methods offer the best results with the least disadvantage.

In this manner, the results of the surgery may be constantly improved by using an iterative and evolving process that constantly incorporates new empirical and theoretical data. Furthermore, since the incision locations are precise, the surgeon can employ various instruments and techniques for precise incision placement. For example: 1) blood vessels in the episclera can be used for alignment by detecting their position on the Corneal topography map, thereby detecting their position relative to the dioptric power function; 2) certain devices exist for this purpose, such as Arcutome by Storz Company (Storz Instrument GmbH, Heidelberg, Germany)

C. Factors to Consider

A tremendous amount of factors may be considered in deciding where to place corrective incisions. The best methods for employing these factors can only be determined after long-term empirical data is gathered. Currently, several factors and their respective impact have been identified. These factors are identified because they are at least potentially quantifiable. Therefore they may incorporated into a quantifiable method based on their known or observed effects.

i. Factors based on the dioptric power function
  1) Area Under the Curve.
  2) Inflection points.
  3) High Frequency If the frequency of the dioptric power curve is too high (approaching 2 within 360 degrees) then the eye may not benefit from surgery because the irregularities are too great.

ii. Patient factors
  1) Maximum pupil size.

The maximum pupil size of an eye is relevant in determining the minimum radius from the center of the cornea where an incision can be made without interfering with vision. For example if the pupil can expand to 6 mm, then any cuts made inside of a 3 mm radius will interfere with vision, at least when the pupil is fully opened.

While this invention applies to all radii (all zones of the eye), one skilled in the art will recognize that the methods of this invention may incorporate a factor which indicates that incisions that interfere with vision are less desirable. Furthermore, in one embodiment of the invention it is preferred to make incisions at a radius of 4 mm (8 mm optical zone).

2) Age of patient

The age of a patient may influence a method of refractive surgery because elasticity of the cornea changes with age. Therefore, the invention contemplates the use of the patient's age as a factor for determining size and location of incisions.

3) Sex of patient

Generally, the cornea's response to outside stimulus varies with the hormone level of the patient. Therefore, the patient's sex is a relevant factor in the planning of corneal surgery. Furthermore, hormone levels vary with respect to several other circumstances. For example, hormone levels will change throughout a women's menstrual cycle, through stages pregnancy or through age. To the extent that the levels may be quantified, each factor bearing on hormonal change may be used to plan refractive surgery.

4) Corneal thickness

When shaping the cornea through incision, it is desirable to make incisions as deep as possible without causing perforation. The depth of an incision should be at least 70 percent of the width but a more desirable depth is 95 percent of total width. Therefore, corneal thickness is a factor that bears on refractive surgery because the preferred depth of an incision may be calculated as a percentage of the overall depth. This is especially true where corneal thickness varies across the corneal surface.

5) Axial length

The eye's axial length is indicative of the shape characteristics of the overall globe of the eye. Relative to refractive surgery, generally, the axial length is indicative of the chances for a successful surgery. For example, large globes (longer axial lengths) may indicate complications that will prevent optimal surgical results. Therefore, axial length is a factor that should be considered in planning refractive surgery.

6) Ratio of horizontal limbus diameter to vertical limbus diameter

Generally, the ratio of horizontal to vertical limbus diameter bears on the generation and characteristics of an astigmatism. Therefore, this ratio is an appropriate factor to influence techniques for astigmatic correction.

7) Ratio of corneal surface area to limbus diameter

The ratio of corneal surface area to limbus diameter is indicative of the cornea's reaction to incisional correction. For example, a large surface area and a small limbus diameter indicates a larger or more full knee of the eye; a small surface area and a large limbus diameter indicates a smaller or less full knee of the eye. This ratio is therefore, an appropriate factor for consideration during surgical planning.

8) Intraocular pressure (IOP)

Varying pressure behind the cornea can change the effect of a corneal incision. Therefore, when planning refractive surgery, the size or location of an incision may be varied depending upon the IOP.

D. Specific Embodiments i. Mean dioptric power value between neighboring astigmatic axes.

The astigmatic cornea generally has opposite steeper astigmatic radii that do not necessarily coincide into one and the same meridian. Therefore, in correcting the astigmatic cornea, some success may be achieved by disposing arcuate cuts asymmetrically, according to the disposition of the steeper semimeridians. However, this process involves a detailed analysis of corneal topography. See Binder P. S., Waring G. O. III, "Keratotomy for astigmatism," *Refractive Keratotomy for Myopia and Astigmatism,* St. Louis, Mo., Mosby—Year Book Incorporated, 1092, 1992.

The type of surgery described above may be implemented using the following general procedures: 1) plotting the dioptric power curves along the circular zones which may be considered appropriate for the arcuate cuts localization; 2) determination of the astigmatic axes position in each selected circular zone; and 3) finding the position of the points with the mean dioptric power value between the neighboring astigmatic axes. The latter points determine the advised position of the ends of the arcuate cuts.

More specifically, the following steps may be performed in order to yield a group of acceptable choices for incision location.

Figure 5:
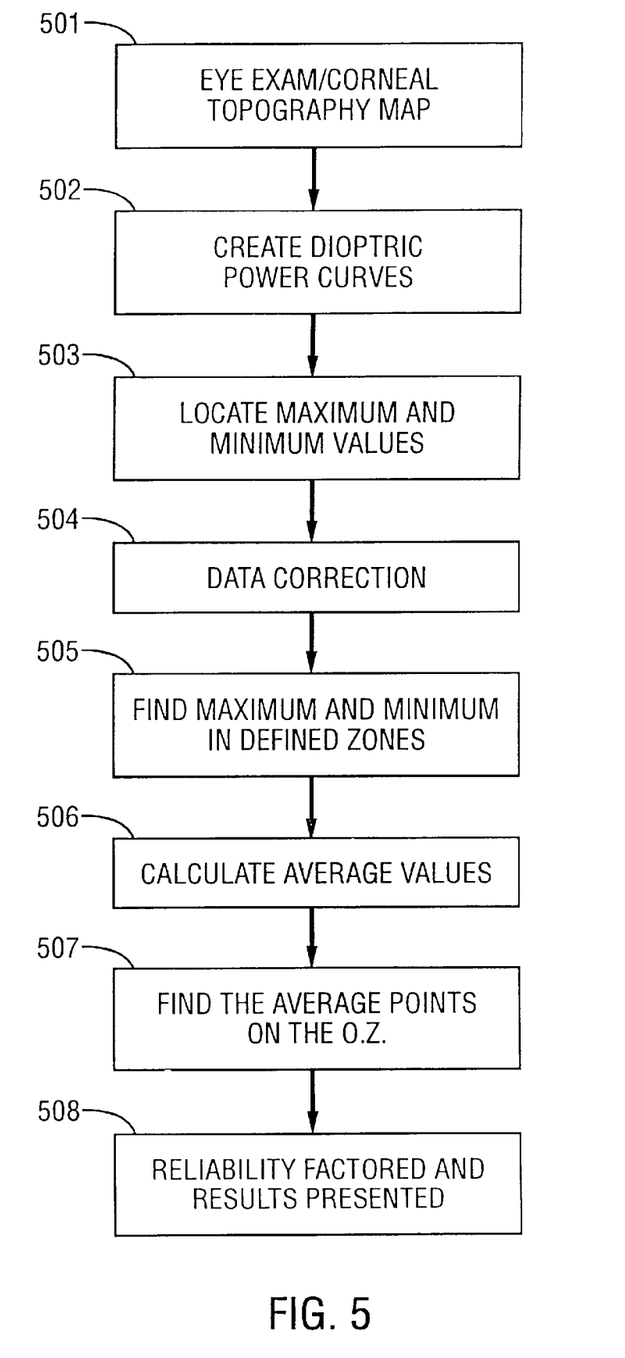
FIG. 5 is a method of the current invention.

Referring to FIG. 5, the block 501 begins the procedure with an eye examination that yields a high resolution corneal topography map. Control proceeds to block 502 where dioptric power curves should be created. The dioptric power curves should be plotted using data from the map taken along the circular zones of preselected diameter values, which may be considered appropriate for the arcuate cuts localization. For example, dioptric power curves might be created for 4 mm oz, 5 mm oz and 6 mm oz (as in FIGS. 1, 2 and 3 respectively).

Control passes to block 503 where the local maximums and minimums of the dioptric power function are located. If a computer program is used, these maximums and minimums can be displayed on a coordinate map (chart) like those shown in FIGS. 6 and 7. Color and size characteristics can be used to express relative values. The chart can be plotted in the same scale as the corneal topography map so that superposition is possible at any stage of data assessment.

Figure 6:
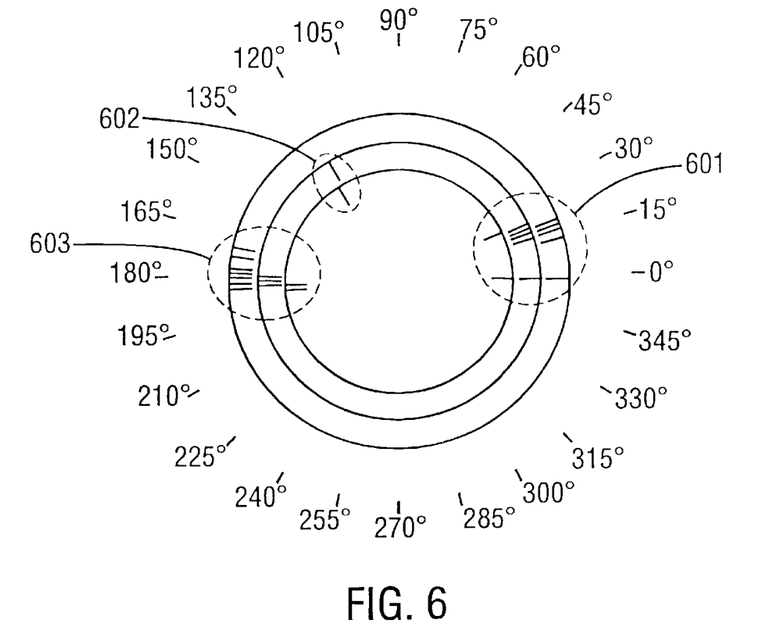
FIG. 6 is a representation of dioptric values by sector.
Figure 7:
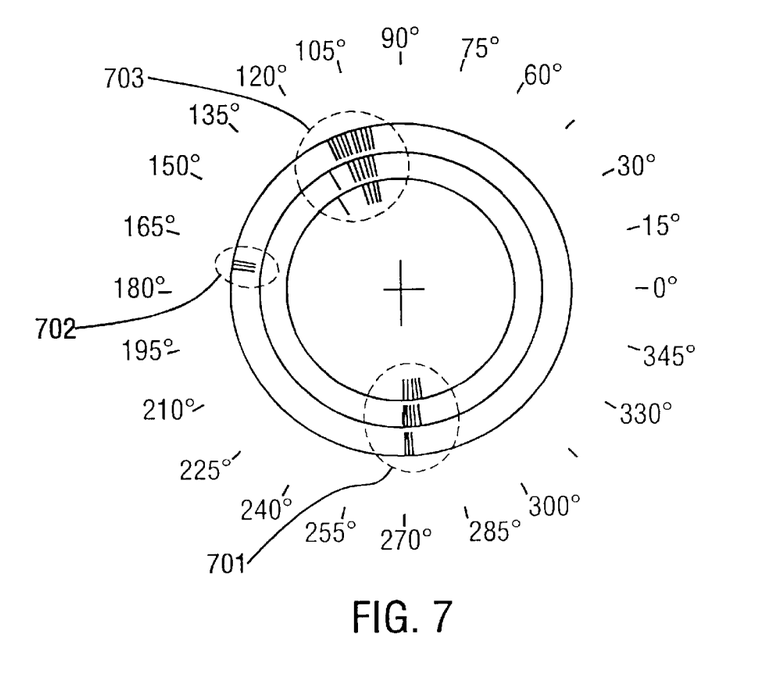
FIG. 7 is a representation of dioptric values by sector.

Control passes to block 504 for correction of the data representation obtained at block 503. The step is performed to accomplish two possible tasks: 1) to exclude data artifacts which might occur at the measurement stage; and 2) to assess and possibly alter the strategy of further data assessment. If a computer is used, the operator or program defines, for each oz, sectors that contain relevant diopter values (see FIGS. 6 and 7). When the process or program continues, it should then exclude any values found outside of the defined sectors. For example FIGS. 6 defines sectors 601 and 603 for the relevant data representing flatter portions of the cornea and sector 602 for anomalous data; FIG. 7 defines sectors 701 and 703 for the relevant data representing steeper portions of the cornea and sector 702 for anomalous data; all data in FIGS. 6 and 7 is obtained from the same oz on the corneal topography map. This exclusion of anomalies and additional unnecessary data increases the accuracy and reduces the complexity of the procedure. Useful information for identifying anomalous and unnecessary data comprises: 1) the chart with local maximum and minimums found at stage 503 (FIG. 3); 2) the corneal topographic map; and 3) a captured image of the Placido rings projected on the cornea.

Pass control to block 505 where the procedure must identify the data points with maximum dioptric power and minimum dioptric power. The only data evaluated here is data that was defined in a sector at block 504. For example, referring to FIG. 6, data in sectors 601 and 603 would be evaluated to find minimum dioptric value (minimum is sought because this is the chart for the flatter values); referring to FIG. 7, data in sectors 701 and 703 is evaluated to find the maximum dioptric value (maximum is sought because this is the chart for the steeper values). At this stage a maximum or minimum (whichever is appropriate) is located for each defined sector.

Control passes to block 506 where a calculation is made to determine, for each oz, the average value of: 1) the maximum value found in the steeper defined sector; and 2) the minimum value found in the flatter defined sector.

Control passes to block 507 where, for each oz, the procedure locates points on the specific oz that have a dioptric value equal to the average value located at block 506 for the same oz. The points in the corneal topographic map, which are characterized by the average dioptric power value, indicate the places where the ends of the arcuate cuts are proposed to be located.

Control passes to block 508 where data such as reliability of keratometric measurements is factored into the results (see Koch D.D. supra; Tsilimbaris M. K., Vlachonikolis I. G., Siganos D. S., Makridakis G. S., Pallikaiis I. G., "Comparison of Keratometric Readings as Obtained by Javal Ophthalmometer and Corneal Analysis System (EyeSys)," *Refract Corneal Surg,* 7: 368–373, 1991. Then the procedure suggests a solution for each oz originally selected for data assessment, i.e. for different values of radial distance from the vertex, at which the arcuate cuts may be performed. It also indicates the most appropriate radial distance for an arcuate cut, from the standpoint of reliability of keratometric measurements. (after correction performed at block 504, non-selected data is considered extraneous).

It should be stressed that this particular procedure suggests all possible dispositions it has found for the arcuate cuts. The final choice of where to cut is left upon the surgeon, who is supposed to select the number and position of the incisions among the suggested alternative ones.

The specific embodiment and technique, described here is further described in a paper, written and yet unpublished: Pallikaris, I. G., Xirafis, M. E., Naoumidis, L. P., "Computer- Disposed Astigmatic Arcuate Cuts Performed with the Help of a Novel Keratome (Arcutome)." That paper is included in this application in appendix ii. Asymmetrical Arcuate Corrective Incisions 1. The concept of asymmetry Referring to FIG. 3, the general shape of the dioptric power function is clinically typical. The typical characteristic referred to is the asymmetry of the peak dioptric values. Physically, this implies that the astigmatism is not symmetric and is greater in one quadrant of the cornea than the opposite worse on one side of the cornea. Specifically, FIG. 3 shows that at 100 degrees, the refractive power is 46. On practically the other side of the eye (170 degrees displaced), at 270 degrees the refractive power is 48.5.

Current standard astigmatic Keratotomy calls for two pairs of arcuate incisions, one pair displaced from the other by 180 degrees over the center of the cornea. For example, Referring to FIG. 8, if each incision 801 is 25 degrees in length, then there is a total incision length of 50 degrees on each side of the cornea. It could also be said that there is 100 degrees of incision length on the whole cornea. See FIG. 8.

Figure 8:
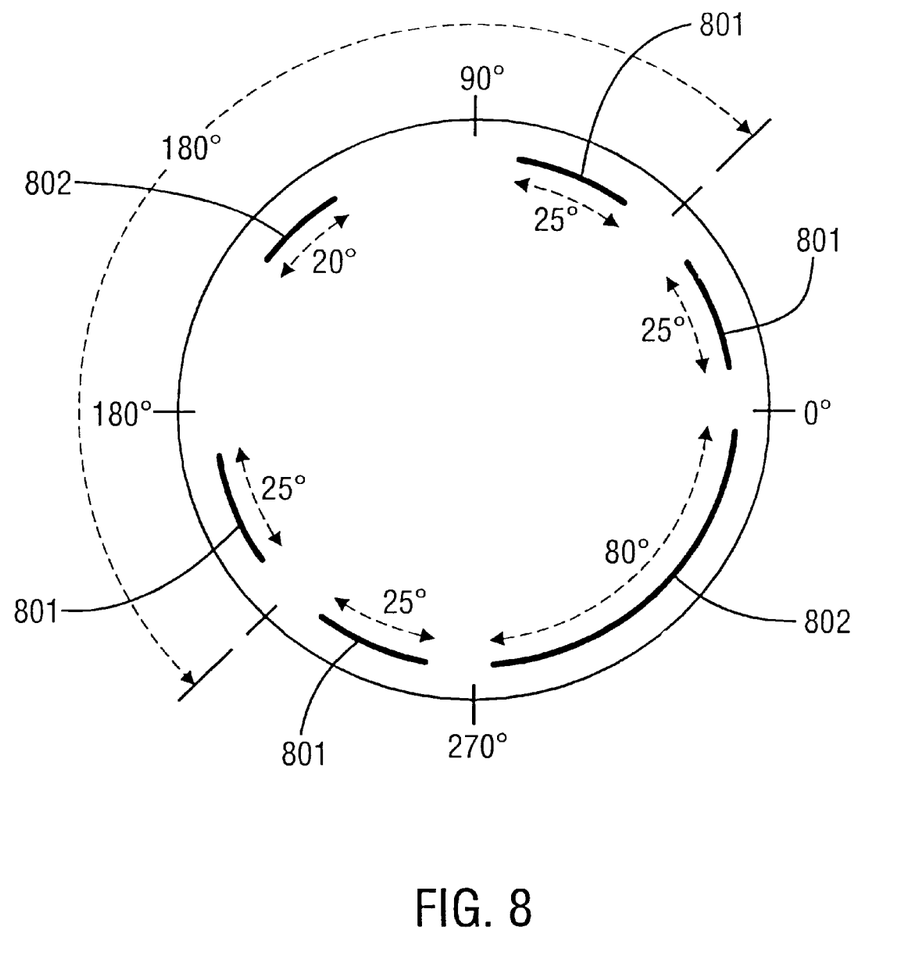
FIG. 8 is illustrative of incision locations.

These embodiments of the invention contemplate the use of asymmetric incisions to correct asymmetric anomalies. Technically, this theory relies on the premise that topographic asymmetry can be correlated with asymmetry of correction. Using the example above, the total incision length of 100 degrees can be distributed among incisions 802 in an asymmetric fashion.

Following the premise of this embodiment, the asymmetrical distribution of the corrective incisions should depend upon the asymmetrical distribution of the astigmatism. For example, if 75% of the steepness is on one side you would have 75% of the total incision length on that side.

2. Imposing a quantitative approach to asymmetric corrections—Area under the curve.

Figure 9:
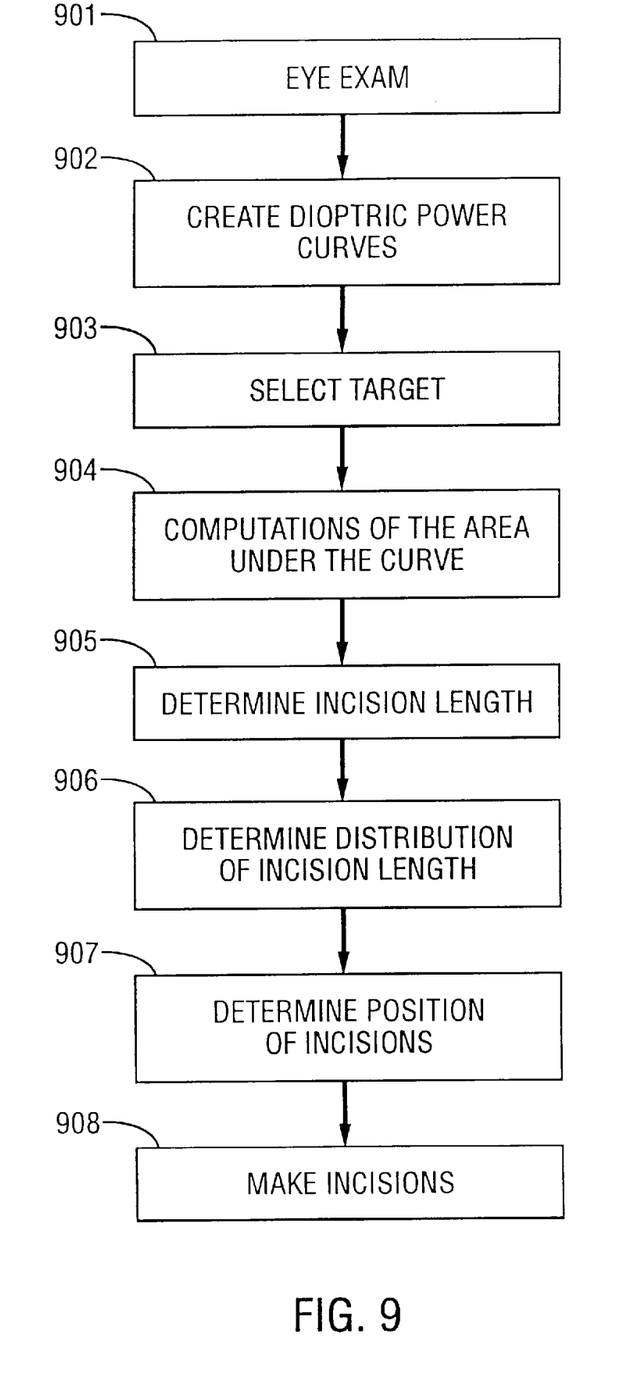
FIG. 9 is a method of the current invention.

The principles of asymmetry described above may be applied in a method that imposes the quantitative or repeatable characteristics described earlier. One method of quantifying the asymmetric approach is to use the area under the dioptric power curve. The steps of the method are as follows:

Referring to FIG. 9, the block 901 begins the procedure with an eye examination that yields a high resolution corneal topography map. Control proceeds to block 902 where dioptric power curves should be created.

Passing control to block 903, a target refractive power is selected. The target is selected based upon the surgeon's goals and the factors know in the art, some of which have been discussed earlier.

Figure 10:
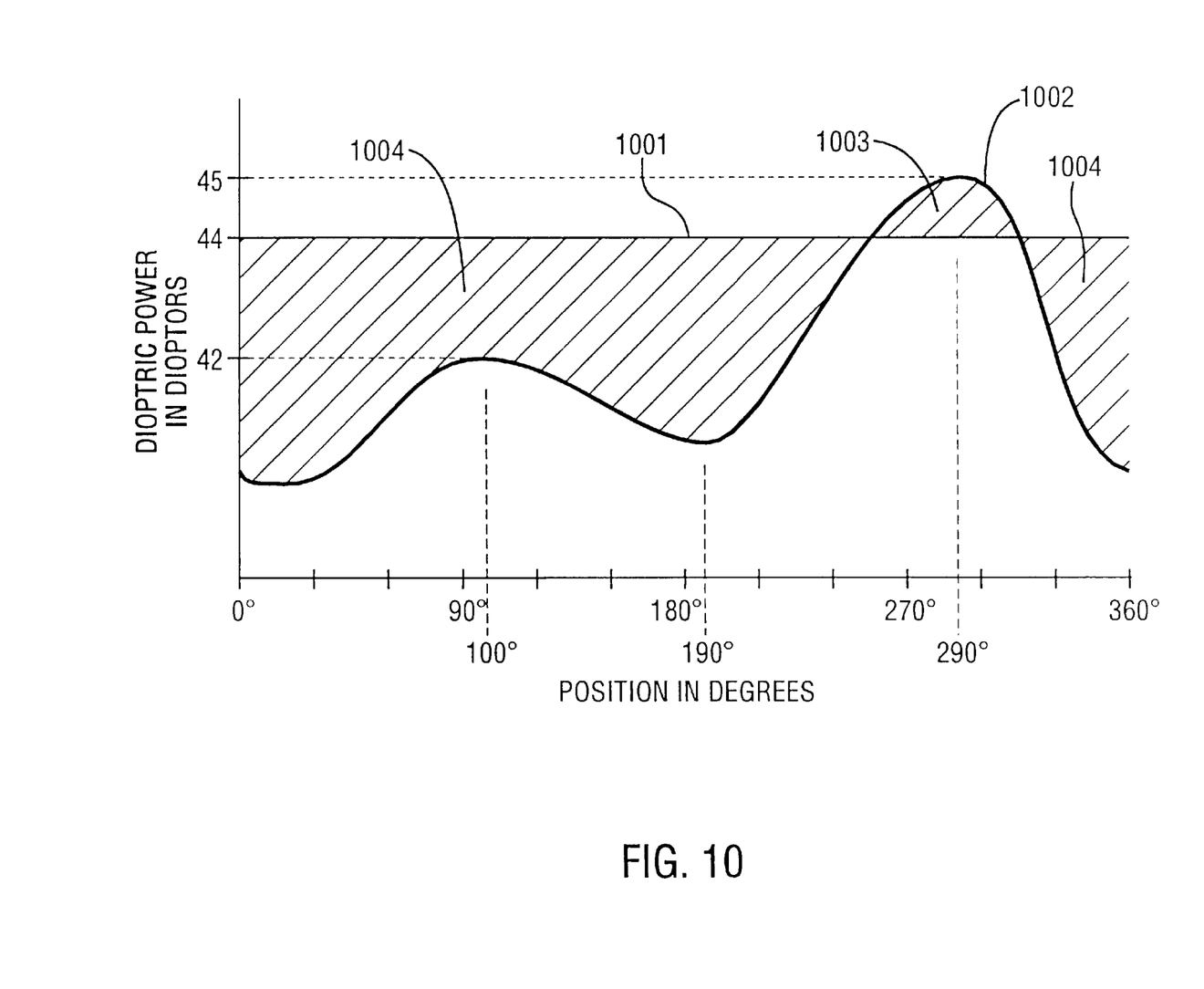
FIG. 10 is a dioptric power curve.
Figure 11A:
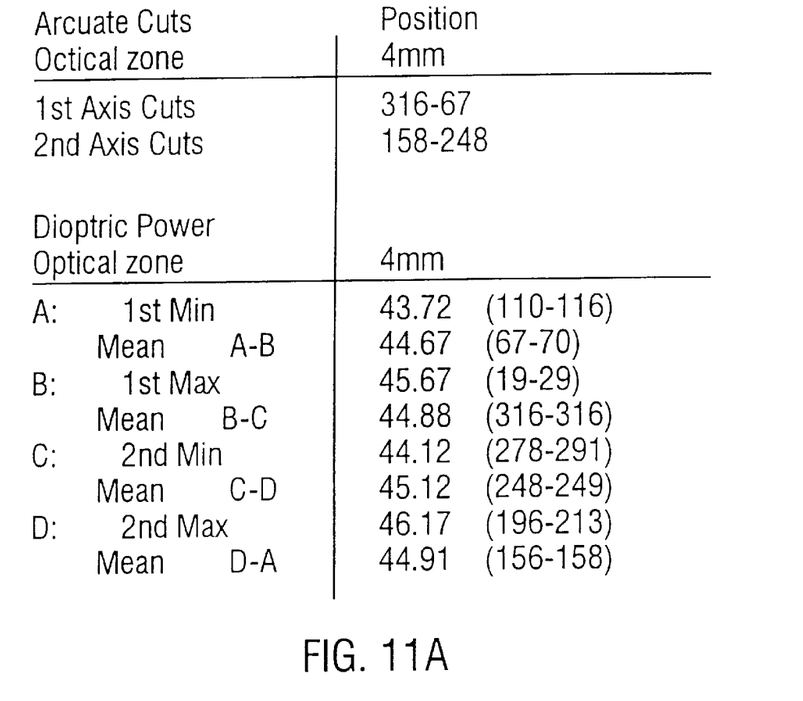
FIG. 11 is an output product of a computer software of the invention.
Figure 11B:
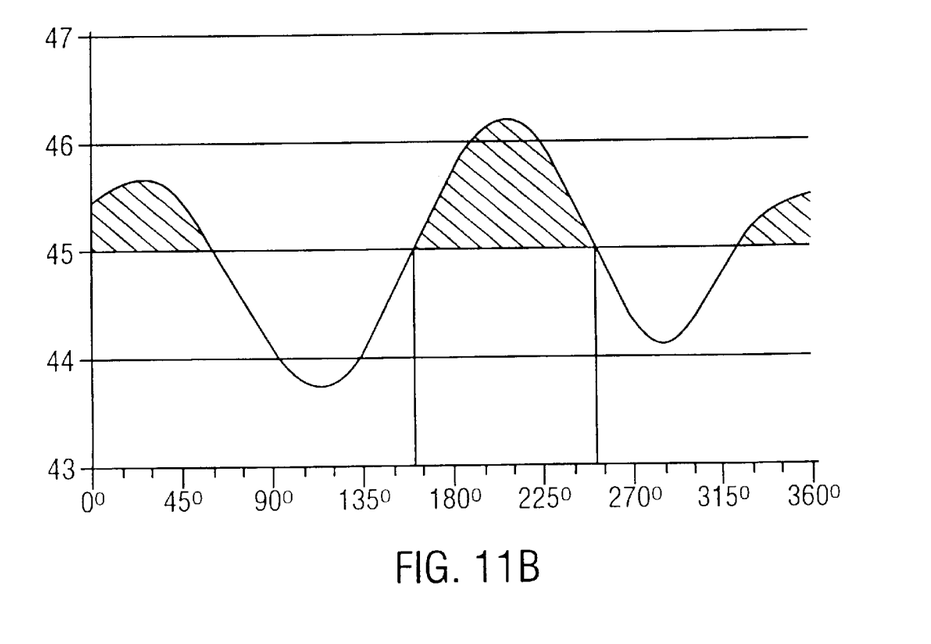
Figure 11C:
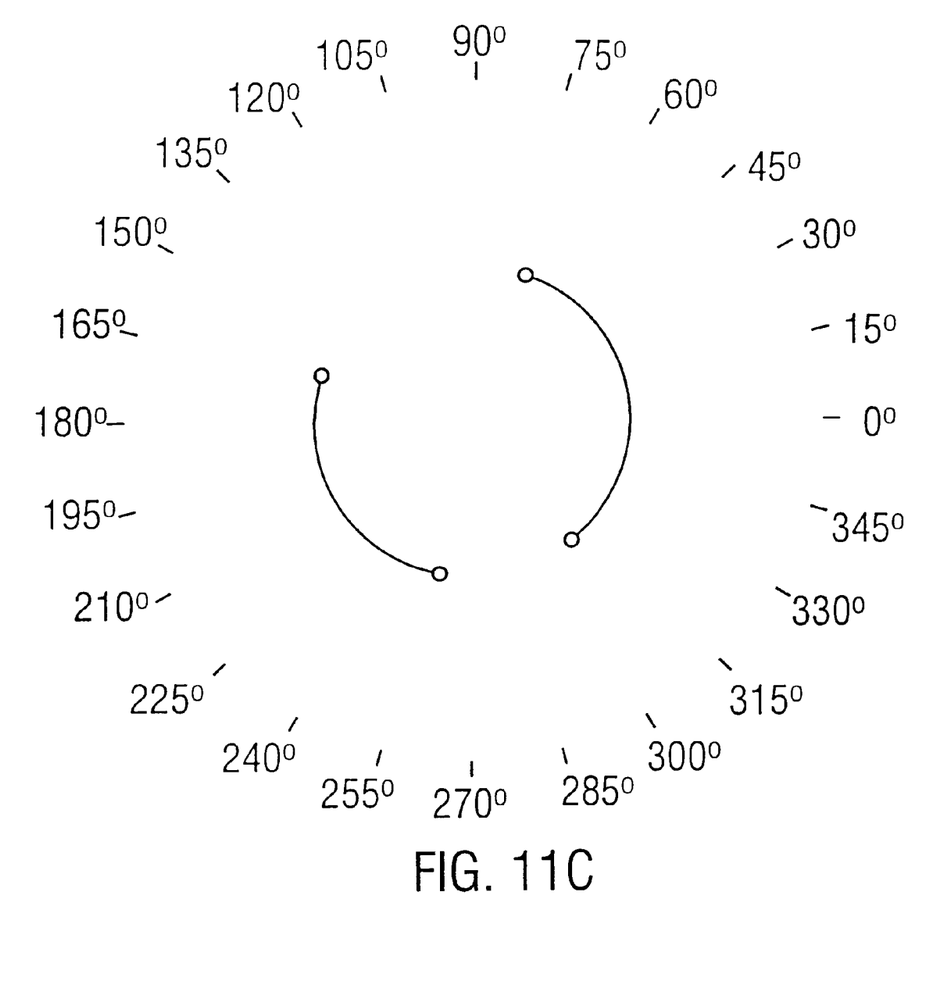
Figure 12A:
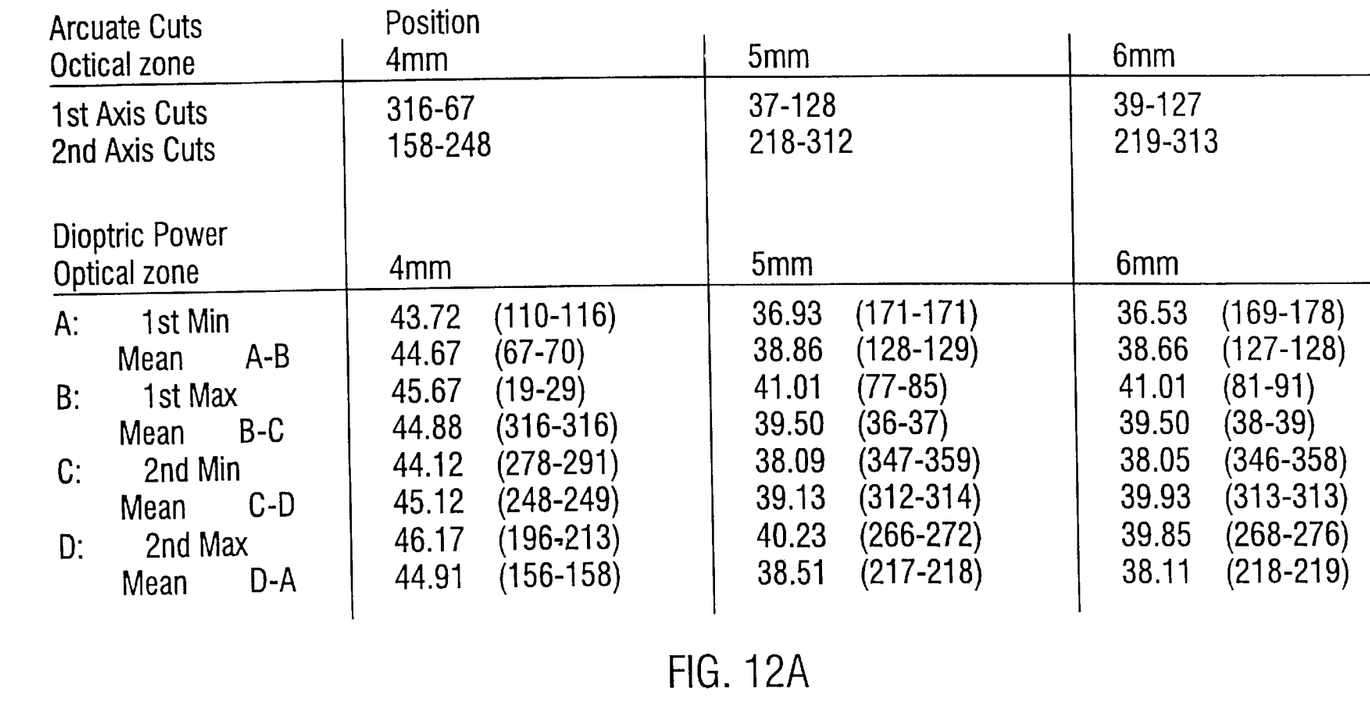
FIG. 12 is an output product of a computer software of the invention.
Figure 12B:
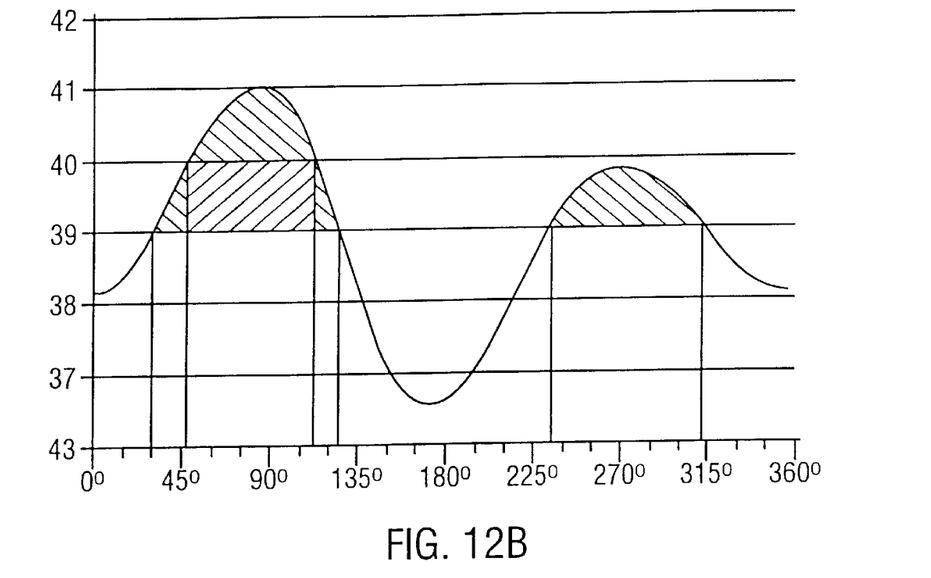
Figure 12C:
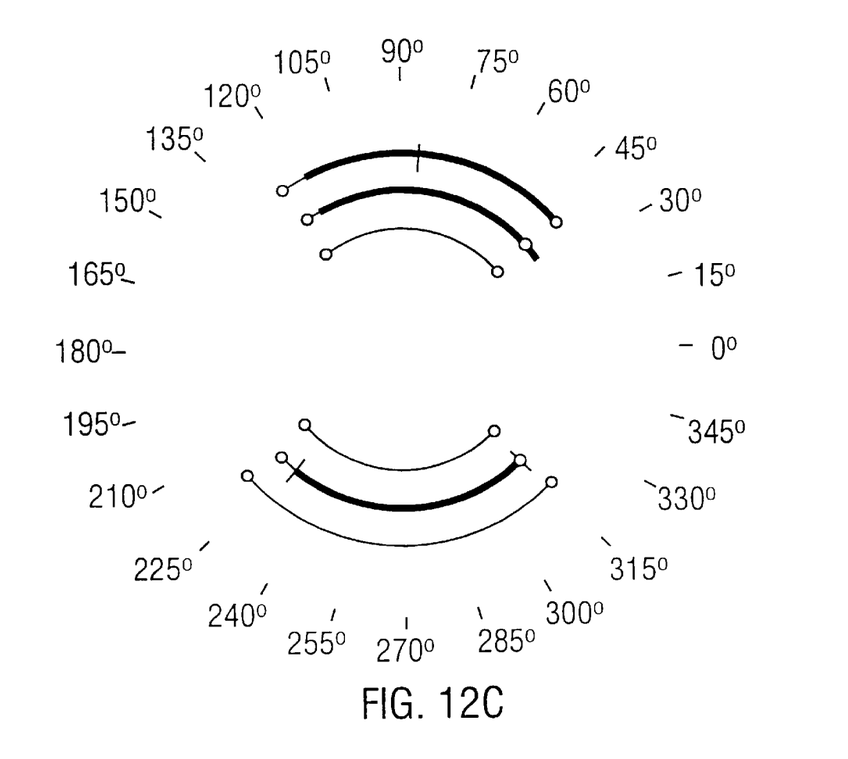

Control passes to block 904 for computation of the area under the curve. Referring to FIG. 10, there is shown a dioptric power curve 1002. For illustrative purposes, suppose that a target of 44 diopters has been selected at block 903. The target can be indicated by a horizontal line 1001 across the dioptric power curve 1002. The calculations that must be made are: 1) the area 1003 that is both under the power curve 1002 and above the target line 1001 (shaded vertically); and 2) the area 1004 that is both beneath the target line 1001 and above the power curve 1002 (shaded diagonally).

Control passes to block 905 where the total incision length must be determined. The length can be calculated using the factors described earlier. Each factor may bear on length, depending upon position of the incision. The factors represent quantitative and fixed gauges that may be correlated to incision length. Therefore, this method step can incorporate data from previous iterations of the method. Some or all of that data may actually be processed during this method step or that data may be incorporated before the design of this method step.

Control passes to block 906 where the distribution of incision length is determined. The length of incision made on the steeper side of the cornea is determined by multiplying (the total length) by (the area 1003) and dividing by (the area 1004). The length of incision to be made on the flatter side of the cornea is determined by multiplying (the total length) by (the area 1004) and dividing by (the area 1003). The factors discussed above and as described at block 905 may influence the distribution of the incision length.

Control passes to block 907 where the incision positions are determined. The radial position of the incision is determined by reference to the diameter of the circular zone (oz) of the relevant dioptric power curve. Consideration of the factors as discussed in step 905 may also bear on the position of the incisions.

Control passes to block 908 where the incisions are made in any acceptable surgical procedure. The invention focuses on arcuate incisions for the correction of astigmatism. However, the invention also contemplates the use of radial or other shaped incisions to the extent directed by the iterative quantitative method here disclosed.

3. Imposing a quantitative approach to asymmetric corrections—Inflection points.

The principles of asymmetry described above may be applied in another method that imposes the quantitative or repeatable characteristics described earlier. This method analyzes the inflection points on the dioptric power curve. Generally, an inflection point is a point along a dioptric power curve where the slope of the curve changes sign. Practically, this can be considered the region where the bend in the curve begins. A method that exploits this principle would follow the same steps as the method for the "area under the curve" technique except for the basis of determining the distribution of incision length. Here, the distribution of total incision length would depend upon the characteristics of the inflections in the dioptric power curve. Quantifying the distance between inflection points on the curve and the area under the curve between the inflection points may determine the length of incision needed or if multiple arcuate incisions are needed.

4. Imposing a quantitative approach to asymmetric corrections—Improving the foregoing techniques.

If the techniques above ("area under the curve" and "inflection point") yield an incision length that exceeds the area of steepness, then the incision may be divided and pair of incisions may be used instead. Therefore, the ratio of area under the opposing curves, ie. on opposite sides of the astigmatism, may indicate the need for unilateral, asymmetric or multiple arcuate incision patterns.

iii. Combinations

The invention contemplates a method that could analyze a given eye disorder using any technique known or presented here. For example, the target power might lie totally outside of the dioptric power curve. The method should then correct the astigmatism and the residual myopia. The techniques used could be chosen from a library. A solution for each technique should obtained and then each solution should be simulated. The method can then suggest the best solution or solutions to the surgeon.

iv. Specialized Software

One illustrative embodiment of a method in accordance with the invention is computer program. Such a program is discussed in the Pallikaris paper (appendix A). The program discussed in Appendix A has been implemented and the source code is submitted as part of this application in appendix B.

In the interest of clarity, not all features of an actual implementation are described in this specification. It will of course be appreciated that in the development of any such actual implementation (as in any software development project), numerous programming decisions must be made to achieve the developers' specific goals and subgoals (e.g., compliance with system- and business-related constraints), which will vary from one implementation to another. Moreover, attention will necessarily be paid to, e.g., proper serialization to handle concurrent events. It will be appreciated that such a development effort might be complex and time-consuming, but would nevertheless be a routine undertaking of program development for those of ordinary skill having the benefit of this disclosure.

v. Non-limitation

It will be appreciated by those of ordinary skill having the benefit of this disclosure that numerous variations from the foregoing illustrations will be possible without departing from the inventive concept described herein. For example, those of ordinary skill having the benefit of this disclosure will recognize that logical functions described above as being implemented in software can equivalently be implemented in hardware, e.g., through the use of discrete logic circuitry, and vice versa.

Accordingly, it is the claims set forth below, and not merely the foregoing illustration, which are intended to define the exclusive rights claimed in this application.

What is claimed is:

1. A Method of refractive surgery which comprises forming incisions at various locations in the cornea the method of refractive surgery comprising:

examining an eye with a corneal topographer to obtain at least some corneal topography data;

selecting appropriate optical zones and constructing correlative dioptric power curves based on the at least some corneal topography data;

locating locations for incisions in the cornea in accordance with the data of the dioptric power curves and forming the incisions at the incision locations to perform the refractive surgery.

2. The method of claim 1 further comprising evaluating one or more patient factors and wherein the incisions are located on the cornea in accordance with the dioptric power curve and the one or more patient factors.

3. A method of refractive surgery comprising:

examining an eye with a corneal topographer to obtain corneal topographic data;

creating dioptric power curves along appropriate optical zones based on the corneal topography data;

deciding total length and location distribution of corrective incisions; and executing the incisions.

4. A method of claim 3 where said total length and location distribution of corrective incisions is decided based upon a mean dioptric power value between neighboring astigmatic axes.

5. A method of claim 3, further comprising performing an area under the curve analysis of the corneal topography data and where said total length and location distribution of corrective incisions is decided based upon an area under the curve analysis.

6. A method of claim 3 further comprising performing an inflection point analysis of the corneal topography data so that the total length and location distribution of corrective incision is analyzed by inflection point where the total length and location distribution of corrective incisions is decided based upon an inflection point analysis.

* * * * *